United States Patent [19]

Mesch

[11] Patent Number: 4,719,309

[45] Date of Patent: Jan. 12, 1988

[54] PREPARATION OF IMIDAZOLES

[75] Inventor: Walter Mesch, Ludwigshafen, Fed. Rep. of Germany

[73] Assignee: BASF Aktiengesellschaft, Ludwigshafen, Fed. Rep. of Germany

[21] Appl. No.: 801,569

[22] Filed: Nov. 25, 1985

[51] Int. Cl.[4] ............................................ C07D 233/58
[52] U.S. Cl. .................................................... 548/335
[58] Field of Search ........................................ 548/335

[56] References Cited

PUBLICATIONS

K. Hofmann, The Chemistry of Heretocyclic Compounds, Imidazole and Its Derivatives, Part I, p. 33 (1953).

Primary Examiner—Henry R. Jiles
Assistant Examiner—Kurt G. Briscoe
Attorney, Agent, or Firm—John H. Shurtleff

[57] ABSTRACT

Imidazoles are prepared by subjecting an $\alpha,\beta$-dicarbonyl compound to a Radziszewski reaction with an aldehyde and ammonia and then catalytically hydrogenating the product.

Imidazole and its derivatives are useful intermediates for drugs, crop protection agents and dyes.

20 Claims, No Drawings

PREPARATION OF IMIDAZOLES

The present invention relates to an improved process for the preparation of imidazoles by subjecting an $\alpha,\beta$-dicarbonyl compound to a Radziszewski reaction with an aldehyde and ammonia.

The preparation of imidazole and of imidazoles substituted in the 2-, 4- and 5-position by the Radziszewski method (cf. Radziszewski, Chem. Ber. 15 (1883), 1493; Ullmanns Enzyklopädie der techn. Chemie, 4th edition, volume 13, page 173 (1977) and K. Hofmann: The Chemistry of Heterocyclic Compounds, Imidazole and Its Derivatives, Part I, page 33, 1953) takes place in accordance with the following equation:

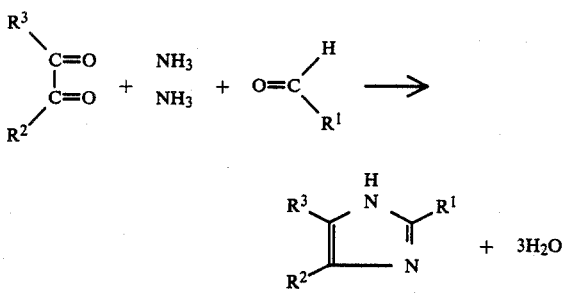

where $R^1$, $R^2$ and $R^3$ are each alkyl, aryl or H.

A substantial disadvantage of this reaction is that it produces large amounts of nonvolatile, resinous, viscous by-products which reduce the yield, make it more difficult to isolate the pure imidazoles and have to be disposed of.

It is an object of the present invention to improve the preparation of imidazoles in such a way that the amount of by-products is greatly reduced.

We have found that this object is achieved, and that imidazoles can be particularly advantageously prepared by reacting an $\alpha,\beta$-dicarbonyl compound with an aldehyde and ammonia, if the crude reaction mixture obtained after the reaction is subjected to catalytic hydrogenation directly or after replacing the solvent.

Suitable $\alpha,\beta$-dicarbonyl components are compounds of the general formula

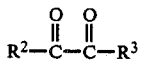

where $R^2$ and $R^3$ are identical or different and are each straight-chain or branched alkyl of 1 to 10, in particular 1 to 5, carbon atoms, aryl of 6 to 10 carbon atoms or hydrogen, eg. ethylglyoxal, methylglyoxal, butane-2,3-dione or benzil. It is particularly advantageous to use glyoxal for the novel process, the glyoxal expediently being employed in the form of an aqueous solution, eg. a 40% strength solution.

Aldehydes which are suitable for the condensation are those of the general formula $R^1CHO$, where $R^1$ is straight-chain or branched alkyl of 1 to 10, in particular 1 to 5, carbon atoms or aryl of 6 to 12 carbon atoms, eg. methyl, ethyl, propyl, isopropyl, butyl, isobutyl, tert.-butyl, pentyl, isopentyl or phenyl. A particularly great increase in the yield of imidazole is obtained when the Radziszewski synthesis is carried out using formaldehyde, which is advantageously employed in the form of an aqueous solution, eg. a 30–40% strength solution.

The reaction of the three reactants is carried out in a conventional manner, the $\alpha,\beta$-dicarbonyl compound, the aldehyde and ammonia generally being combined in a molar ratio of 1:1.0–2.5:1.5–5, advantageously 1:1.0–1.5:2.0–3.5. The reaction is carried out as a rule at from 40° to 100° C., in particular from 50° to 80° C., in the course of from 2 to 6 hours.

The reaction mixture obtained when the reaction is complete is as a rule used directly for the hydrogenation. It is frequently advantageous to replace the solvent before the hydrogenation, this being done, for example, by extracting the aqueous reaction mixture with an organic solvent. The extraction is advantageously carried out using a solvent which is very poorly water-soluble, readily dissolves the reaction products, such as imidazoles or their intermediates, and is inert in the subsequent hydrogenation step. Particularly suitable compounds in this connection are fairly long-chain amines, such as dibutylamine, ethers, such as diethyl ether or methyl tert.-butyl ether, and especially higher alcohols of 4 to 8 carbon atoms, eg. isobutanol, butanol, pentanol, isopentanol or cyclohexanol.

Advantageously, the solvent is used in an amount of from 20 to 300, preferably from 50 to 200, % by weight, based on the $\alpha,\beta$-dicarbonyl compound.

The reaction with hydrogen is carried out in the presence of a hydrogenation catalyst by a conventional continuous or batchwise method. Suitable catalysts are the commonly used hydrogenation catalysts, for example those which contain nickel, cobalt, silver, platinum, palladium and/or copper. Catalysts without a carrier, eg. Raney nickel or Raney cobalt, or supported catalysts can be used. The catalysts without a carrier may furthermore be compounds of the stated metals, preferably their oxides. Examples of suitable carriers are silica, aluminum silicate, alumina and carbon. Advantageous catalysts are palladium on active carbon or alumina in the form of moldings, copper on alumina, or Raney nickel. In the batchwise procedure, from 0.05 to 5.0, preferably from 0.05 to 2, % by weight, based on the $\alpha,\beta$-dicarbonyl compound used, of the suspended catalyst are added. Where hydrogenation is carried out by continuous procedure, the catalyst, preferably in the form of firmly bound pieces, is initially taken in a pressure reactor through which the reactants flow.

The hydrogenation is advantageously carried out at above 30° and below 400° C., advantageously from 50° to 300° C., in particular from 120° to 200° C., under a hydrogen pressure of from 10 to 350, preferably from 20 to 250 bar.

As a rule, the reaction time for the hydrogenation is from 2 to 5 hours. In the continuous procedure, this corresponds to the reciprocal of the feed volume per unit time, relative to the free reactor volume.

In the batchwise procedure, the imidazoles are generally isolated from the mixture emerging from the hydrogenation by separating off the catalyst, for example by filtration, and subjecting the reaction mixture to fractional distillation, or, if necessary, first extracting the imidazoles and then subjecting the extract to fractional distillation. The distillation is carried out by a conventional continuous or batchwise method, under atmospheric or superatmospheric pressure.

Using the novel process, the yields are increased by as much as 15%.

Imidazoles and their derivatives are useful intermediates for drugs, crop protection agents and dyes.

EXAMPLE 1

An aqueous solution of 40% strength glyoxal, 37% strength formaldehyde and 19% strength ammonia in a molar ratio of 1:1:3 is reacted at 60° C. in the course of 3 hours.

The resulting crude brown imidazole solution is then worked up by distillation, this being done by first distilling off unconverted ammonia and water under atmospheric pressure. The imidazole then distills over at 165° C. under 26 mbar and is obtained in a yield of 69% of theory. The distillation residue corresponds to 38% by weight, based on the imidazole obtained.

EXAMPLE 2

A solution of crude imidazole prepared as described in Example 1 is heated together with 3% by weight of Raney nickel for 4 hours at 200° C. under a hydrogen pressure of 250 bar. The solution, which was previously brown, is then found to be substantially decolorized, and the catalyst is filtered off. Distillation carried out as described in Example 1 gives a yield of imidazole of 79% of theory, and hydrogenated imidazoles are not detectable. The distillation residue has fallen to 10% by weight, based on the resulting imidazole, which has a purity of 99.4% according to gas chromatography.

EXAMPLE 3

A solution of crude imidazole prepared as described in Example 1 is heated for 3 hours at 200° C. under a hydrogen pressure of 30 bar in the presence of 0.5% by weight of a catalyst consisting of 10% of palladium on active carbon.

The filtered colorless solution is distilled as described in Example 1. The resulting colorless imidazole has a purity of 99.2% according to gas chromatography and is obtained in a yield of 84% of theory. The distillation residue has decreased to 9% by weight of pure imidazole, compared with 38% by weight in Example 1.

EXAMPLE 4

(a) A mixture of 1450 g (10 g mol) of 40% strength aqueous glyoxal and 440 g (10 g mol) of acetaldehyde is passed, in the course of 1 hour, into 2550 g (30 g mol) of a stirred 20% strength solution of ammonia in water. The reaction temperature is kept at 40° C. by cooling. The mixture is then heated at 80° C. for 2 hours.

(b) The water is distilled off under atmospheric pressure from 2000 g of the product prepared as described in (a). Further heating under 40 mbar gives 314 g (85% of theory) of 2-methylimidazole. The distillation residue is 78 g of 25% by weight, based on the methylimidazole obtained.

(c) 2000 g of the product prepared as described in (a) are heated in an autoclave for 3 hours at 200° C. with 20 g of a catalyst consisting of 20% of copper on alumina. Hydrogen is injected under a pressure of up to 20 bar. The catalyst is separated off and the hydrogenation product is worked up by distillation to give 340 g (92% of theory) of methylimidazole, in addition to 37 g of residue, corresponding to 11% by weight, based on methylimidazole.

EXAMPLE 5

The crude aqueous solution of imidazole prepared as described in Example 1 is extracted with the same volume of isopentanol in an extractor. The alcoholic extract is worked up by two methods:

(a) Working up 1800 g of extract by distillation in a Claisen apparatus gives isopentanol and 139 g of imidazole having a melting point of 88°-89° C. and a purity of 99.2% according to gas chromatography. The distillation residue is 15 g.

(b) 2% of Raney nickel is added to the extract, which is then kept at 150° C. for 3 hours under hydrogen pressure of 30 bar. Distillation of 1800 g of this hydrogenation product gives 147 g of imidazole having a melting point of 88°-89° C. and a purity of 99.4% according to gas chromatography. The distillation residue is 7 g.

I claim:

1. In a process for the preparation of an imidazole by the Radziszewski reaction in which, using water as a solvent, an $\alpha,\beta$-dicarbonyl compound of the formula

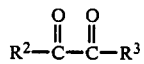

wherein $R^2$ and $R^3$ are alkyl of 1 to 10 carbon atoms, aryl of 6 to 10 carbon atoms or hydrogen, is simultaneously condensed with ammonia and with an aldehyde of the formula

wherein $R^1$ is alkyl of 1 to 10 carbon atoms, aryl of 6 to 12 carbon atoms or hydrogen, the improvement which comprises:

subjecting the crude reaction mixture obtained from the Radziszewski reaction to catalytic hydrogenation either directly or after replacing water with another solvent which is inert to the hydrogenation.

2. The process as claimed in claim 1, wherein the $\alpha,\beta$-dicarbonyl compound used is glyoxal.

3. A process as claimed in claim 1, wherein the hydrogenation is carried out at above 30° C. and below 400° C.

4. A process as claimed in claim 1, wherein the hydrogenation is carried out under a hydrogen pressure of from 10 to 350 bar.

5. A process as claimed in claim 1, wherein the hydrogenation is carried out in aqueous solution.

6. A process as claimed in claim 1, wherein nickel, cobalt, silver, palladium, platinum and/or copper catalysts are used as hydrogenation catalysts.

7. A process as claimed in claim 1, wherein the hydrogenation is carried out in an inert organic solvent selected from the group consisting of alcohols, ethers and long-chain amines.

8. A process as claimed in claim 7, wherein the inert organic solvent is used in an amount of from 20 to 300% by weight based on the $\alpha,\beta$-dicarbonyl compound.

9. A process as claimed in claim 7, wherein the inert organic solvent is an alcohol of 4 to 8 carbon atoms.

10. A process as claimed in claim 8, wherein the inert organic solvent is an alcohol of 4 to 8 carbon atoms.

11. A process as claimed in claim 1, wherein the aldehyde is formaldehyde.

12. A process as claimed in claim 1, wherein the $\alpha,\beta$-dicarbonyl compound is glyoxal and the aldehyde is formaldehyde or acetaldehyde.

13. A process as claimed in claim 12, wherein the crude reaction mixture as an aqueous solution is extracted with an inert solvent which is poorly water-soluble in order to separate a crude imidazole product and subject it to catalytic hydrogenation in said inert solvent.

14. A process as claimed in claim 1, wherein the Radziszewski reaction is carried out to condense glyoxal in aqueous solution with ammonia and with an aldehyde selected from the group consisting of formaldehyde and acetaldehyde, the crude reaction mixture is then extracted with an alcohol of 4 to 8 carbon atoms to replace water with said alcohol as the solvent, and the resulting crude extract is subjected to catalytic hydrogenation at above 30° C. and below 400° C. and under a hydrogen pressure of from 10 to 350 bar, thereafter isolating the imidazole product by fractional distillation.

15. A process as claimed in claim 14, wherein the catalytic hydrogenation is carried out at a temperature of from 50° C. to 300° C. and under a hydrogen pressure of from 20 to 250 bar.

16. A process as claimed in claim 15, wherein the catalytic hydrogenation is carried out at a temperature of from 120° C. to 200° C.

17. A process as claimed in claim 14, wherein the alcohol solvent is used in an amount of from 20 to 300% by weight based on the glyoxal.

18. A process as claimed in claim 14, wherein the alcohol solvent is used in an amount of from 50 to 200% by weight based on the glyoxal.

19. A process as claimed in claim 14, wherein the catalyst used for the hydrogenation is a metal selected from the group consisting of nickel, cobalt, silver, palladium, platinum and copper.

20. A process as claimed in claim 14, wherein the reaction time for the hydrogenation is about 2 to 5 hours.

* * * * *